United States Patent [19]
Gotsu et al.

[11] Patent Number: 5,900,136
[45] Date of Patent: May 4, 1999

[54] METHOD OF MEASURING CONCENTRATION OF NONELECTROLYTE IN ELECTROLYTE SOLUTION, METHOD OF PREPARING MIXED SOLUTION CONTAINING ELECTROLYTES AND NONELECTROLYTES AND APPARATUS FOR PREPARING THE SOLUTION

[75] Inventors: Toshio Gotsu, Saitama-ken; Takeru Shibata, Kanagawa-ken; Yoshihiro Tsuzuso, Saitama-ken; Hiroyuki Suzuki, Saitama-ken; Toshiyuki Nakama, Saitama-ken, all of Japan

[73] Assignees: TOA Electronics Ltd., Tokyo; SciTec Kabushiki Kaisha, Kanagawa, both of Japan

[21] Appl. No.: 09/019,406

[22] Filed: Feb. 5, 1998

Related U.S. Application Data

[63] Continuation of application No. 08/737,912, Nov. 26, 1996, Pat. No. 5,762,769, filed as application No. PCT/JP96/00834, Mar. 28, 1996.

[30] Foreign Application Priority Data

Mar. 29, 1995 [JP] Japan ...................................... 7-70274

[51] Int. Cl.⁶ ...................................................... G01N 27/26
[52] U.S. Cl. ........................ 205/775; 205/777.5; 205/792; 324/439
[58] Field of Search ................................. 205/775, 777.5, 205/789, 792; 324/439

[56] References Cited

FOREIGN PATENT DOCUMENTS 58-71654 10/1983 Japan .
60-155952 8/1985 Japan .
5-502614 5/1993 Japan .

*Primary Examiner*—Bruce F. Bell
*Attorney, Agent, or Firm*—Panitch Schwarze Jacobs & Nadel, P.C.

[57] ABSTRACT

Prior to measuring the concentration of a nonelectrolyte in an electrolyte solution, the electric conductivity of a mixed solution containing electrolytes and the nonelectrolyte is previously measured so as to determine the correlation between the electric conductivity and the concentration of the nonelectrolyte as to the same system. The concentration of the nonelectrolyte in the mixed solution can be determined from the electric conductivity obtained by measuring the mixed solution, based on the correlation.

2 Claims, 10 Drawing Sheets

METHOD OF MEASURING CONCENTRATION OF NONELECTROLYTE IN ELECTROLYTE SOLUTION, METHOD OF PREPARING MIXED SOLUTION CONTAINING ELECTROLYTES AND NONELECTROLYTES AND APPARATUS FOR PREPARING THE SOLUTION

CROSS REFERENCE TO RELATED APPLICATION

This application is a continuation of application Ser. No. 08/737,912, filed Nov. 26, 1996, now U.S. Pat. No. 5,762, 769 which is a PCT/JP96/00834 filed Mar. 28, 1996 entitled "Method of Measuring Concentration of Nonelectrolyte in Electrolyte Solution, Method of Preparing Mixed Solution Containing Electrolytes and Nonelectrolytes and Apparatus for Preparing the Solution," the entire disclosure of which is incorporated herein by reference.

TECHNICAL FIELD

The present invention generally relates to a method of measuring the concentration of a nonelectrolyte in a solution in which one or more electrolytes and one or more nonelectrolytes coexist. Further, the present invention relates to a preparation method and a preparation apparatus capable of preparing a mixed solution containing one or more nonelectrolytes of a given concentration by measuring the concentration of said nonelectrolytes in an electrolyte solution. The present invention is used particularly in the food industry and the pharmaceutical industry and, in particular, effectively used for the measurement of the concentration of a dialysing solution (dialysate) and the preparation thereof in the medical care field.

BACKGROUND ART

Conventionally, an electrolyte such as salt or sodium carbonate and a nonelectrolyte such as sugar or alcohol are often added to and mixed with a polar solvent such as water or the like in the food industry and the pharmaceutical industry. Further, in the medical care field, a water solution in which sodium chloride as an electrolyte, glucose as a nonelectrolyte and other small amounts of components are dissolved is utilized as a dialysate used for a dialysing treatment.

When these products are manufactured, since it is difficult to directly measure the concentration of nonelectrolytes in the solutions the electrolytes and the nonelectrolytes in the solution have conventionally been set to given concentrations, respectively by adding predetermined amounts of electrolytes and nonelectrolytes to a predetermined amount of water or a polar solvent which is calculated to have a given concentrations.

However, in this method, because the electrolytes and the like absorb water and change weight while they are stored and further weighing errors are caused by the vibration of a balance and the like, even if the predetermined amounts of electrolytes and nonelectrolytes are weighed, the concentration of a resulting solution is not accurately made to a given concentration. In addition, each time a necessary amount of the solution is changed, necessary amounts of electrolytes, nonelectrolytes, water and the like must be recalculated.

Further, for example, as to the dialysate, medicines used in the preparation of the dialysis solution have conventionally been divided into a so-called agent A mainly composed of sodium chloride and a so-called agent B composed of sodium hydrogencarbonate and they have been supplied to medical sites as undiluted solutions of given concentrations in a liquid state. Therefore, in the medical sites, the dilution ratios for the thus supplied undiluted solutions of agent A and agent B were calculated based on the respective concentrations and the dialysate was prepared by stirring and mixing predetermined amounts of the respective undiluted solutions with a predetermined amount of diluting water in a preparation tank.

Recently, however, there is a proposal in which the agent A and agent B used in the preparation of the dialysate are supplied in a powder state to medical institutions, and the dialysate having a given concentration is prepared at the medical sites by dissolving these powdered medicines in water, respectively, to make a liquid agent A and a liquid agent B each having a given concentration and thereafter mixing these liquid agents A and B.

Various methods are available to measure the concentration of electrolytes such as sodium hydrogen-carbonate used as agent B, and in particular, an electric conductivity meter is widely used because it has many advantages such as a simple construction, easy handling and high reliability resulting from a lower number of factors by which a measured value is influenced.

Therefore, in the preparation of the dialysate, the concentration of a water solution containing the agent B composed of sodium hydrogencarbonate can be simply measured using the electric conductivity meter or the like. On the other hand, the agent A mainly composed of sodium chloride contains grape sugar (glucose) as a nonelectrolyte in addition to sodium chloride, potassium chloride, calcium chloride, magnesium chloride, sodium acetate etc. as electrolytes. It has conventionally been thought impossible to measure the concentration of the glucose in a water solution containing the agent A using an electric conductivity meter.

That is, the electric conductivity meter is not applicable to nonelectrolytes which are not dissociated to generate ions because the electric conductivity meter uses an electric current flowing through a solution due to the ions generated by the dissociation of substances dissolved in a polar solvent such as water.

Although refractometers, polarimeters and the like are as instruments for directly measuring the concentration of nonelectrolytes in a solution, these instruments are disadvantageous in that they are complex in construction, difficult to handle, have low reliability and measured values are liable to vary depending upon how samples are prepared.

Therefore, concerning the agent A of a dialysate, as described above, predetermined amounts of sodium chloride (electrolyte) etc. and glucose (nonelectrolyte) determined by calculation are added to a predetermined amount of water calculated to have a given concentration, thereby the electrolytes and the nonelectrolyte in the water solution are set to given concentrations, respectively.

Consequently, there arises the same problems as the above in the preparation of the dialysing solution, that is, because the amount of the liquid is increased by the dissolution of the nonelectrolyte, the electrolytes such as sodium chloride etc. and glucose or the like absorb water to change their weight while being stored, as well as weighing errors caused by the vibration of the balance, even if predetermined amounts of electrolytes and glucose are weighed, the concentration of the resulting solution is not accurately set to a given concentration. Furthermore, each time a necessary amount of a solution is changed, necessary amounts of electrolytes, nonelectrolyte, water and the like must be recalculated.

DISCLOSURE OF INVENTION

Taking the above circumstances into consideration, an object of the present invention is to provide a method of directly and accurately measuring the concentration of a nonelectrolyte in a solution which contains electrolytes and nonelectrolytes by using a simple instrument.

Another object of the present invention is to provide a preparation method and a preparation apparatus capable of simply and accurately preparing a mixed solution containing nonelectrolytes of a given concentration by measuring the concentration of the nonelectrolytes in a solution which contains electrolytes and the nonelectrolytes.

Still another object of the present invention is particularly to provide a measuring method capable of directly and accurately measuring the concentration of a nonelectrolyte in the agent A of a dialysate which contains electrolytes and the nonelectrolyte by using a simple instrument, and in addition a preparation method and a preparation apparatus capable of simply and accurately preparing a water solution of the agent A containing a nonelectrolyte of a given concentration, by simply and accurately measuring the concentration of the nonelectrolyte in the agent A using the above method.

In summary, the present invention is a method of measuring the concentration of a nonelectrolyte in an electrolyte solution, comprising the steps of: measuring the electric conductivity of the mixed electrolyte solution containing at least one electrolyte and at least one nonelectrolyte; and determining the concentration of the nonelectrolyte in the mixed solution from the measured electric conductivity based on the correlation between the electric conductivity of the mixed solution and the concentration of the nonelectrolyte determined previously as to the same system. In accordance with an example of the present invention, the electrolyte is an electrolyte medicine mainly composed of sodium chloride and the nonelectrolyte is a glucose medicine.

According to another aspect of the present invention, there is provided a method of preparing a mixed solution, comprising the steps of: adding and mixing at least one nonelectrolyte to and with an electrolyte solution while continuously measuring the electric conductivity of the electrolyte solution; and determining the concentration of the nonelectrolyte added to and mixed with the electrolyte solution from the measured electric conductivity based on the correlation between the electric conductivity and the concentration of the nonelectrolyte determined previously as to the same system, to thereby obtain a mixed solution containing the electrolyte and the nonelectrolyte with the nonelectrolyte set to a given concentration. In accordance with an example of the present invention, the electrolyte solution is an electrolyte water solution mainly composed of sodium chloride and the nonelectrolyte is glucose.

According to another aspect of the present invention, there is provided an apparatus for preparing a mixed solution containing at least one electrolyte and at least one nonelectrolyte, comprising: electrolyte storage means for storing the electrolyte; nonelectrolyte storage means for storing the nonelectrolyte; water supply means for supplying a predetermined amount of water; a preparation tank capable of accommodating and stirring to uniformly mix a predetermined amount of the electrolyte supplied from said electrolyte storage means, a predetermined amount of the nonelectrolyte supplied from said nonelectrolyte storage means and a predetermined amount of the water supplied from said water supply means; and an electric conductivity meter for measuring the concentration of a water solution stirred and uniformly mixed in said preparation tank; wherein after an electrolyte water solution of a given concentration is prepared by supplying the electrolyte and the water into said preparation tank, a given amount of the nonelectrolyte is supplied incrementally from said nonelectrolyte storage means into said preparation tank to thereby prepare a mixed water solution, the concentration of the nonelectrolyte in the mixed water solution is continuously measured by said electric conductivity meter, and the supply of the nonelectrolyte from said nonelectrolyte storage means into said preparation tank is stopped when the value of the concentration reaches a given value. In accordance of an example of the present invention, said apparatus is a preparation apparatus for the agent A of a dialysate, the electrolyte is an electrolyte powder medicine mainly composed of a sodium chloride powder and the nonelectrolyte is a glucose powder medicine.

According to still another aspect of the present invention, there is provided an apparatus for preparing a mixed solution containing at least one electrolyte and at least one nonelectrolyte, comprising: electrolyte storage means for storing the electrolyte; nonelectrolyte storage means for storing the nonelectrolyte; water supply means for supplying a given amount of water; a first preparation tank capable of accommodating and stirring to uniformly mix a given amount of the electrolyte supplied from said electrolyte storage means and a given amount of the water supplied from said water supply means; a first electric conductivity meter for measuring the concentration of an electrolyte water solution stirred and uniformly mixed in said first preparation tank; a second preparation tank capable of accommodating and stirring to uniformly mix the electrolyte water solution of a given concentration supplied from said first preparation tank and a given amount of the nonelectrolyte supplied from said nonelectrolyte storage means; and a second electric conductivity meter for measuring the concentration of the nonelectrolyte in a mixed water solution stirred and uniformly mixed in said second preparation tank; wherein a mixed water solution is prepared by incrementally supplying a given amount of the nonelectrolyte from said nonelectrolyte storage means into said second preparation tank, the concentration of the nonelectrolyte in the mixed water solution is continuously measured by said second electric conductivity meters and the supply of the nonelectrolyte from said nonelectrolyte storage means into said second preparation tank is stopped when the value of the concentration reaches a given value. With an example of the present invention, said apparatus is a preparation apparatus for the agent A of a dialysate, the electrolyte is an electrolyte powder medicine mainly composed of a sodium chloride powder and the nonelectrolyte is a glucose powder medicine. According to another example, the electrolyte contains at least first and second electrolyte components and the electrolyte storage means comprises at least first and second electrolyte storage means for separately storing the first and second electrolyte components, respectively. In particular, said apparatus is a preparation apparatus for the agent A of a dialysate, the electrolyte contains a first electrolyte powder medicine composed of sodium chloride, a second electrolyte powder medicine composed of sodium acetate and a third liquid electrolyte medicine composed of potassium chloride and magnesium chloride as a small amount component, and the nonelectrolyte is a glucose powder medicine.

BEST MODE FOR CARRYING OUT THE INVENTION

First, a method of measuring the concentration of a nonelectrolyte in an electrolyte solution according to the present invention will be described.

A nonelectrolyte such as sugar, alcohol, amino acid is not dissociated to generate ions even if it is dissolved in a polar solvent such as water. Thus, even if electrodes of an electric conductivity meter are put into its solution and a voltage is imposed thereto, no current flows. Therefore, until now it has been thought that not only the concentration of a nonelectrolyte cannot be measured by the electric conductivity meter but also that the correlation between the concentration of the nonelectrolyte and the electric conductivity cannot be obtained.

In the preparation of the agent A of a dialysate, the inventors examined the change of the electric conductivity of an intermediate concentration of electrolyte water solution mainly composed of sodium chloride by sequentially adding and mixing glucose as a nonelectrolyte to and with the electrolyte water solution and continuously measuring the electric conductivity of the electrolyte water solution using the electric conductivity meter. As a result, the inventors found that the detected electric conductivity changed in accordance with the additive amount of the nonelectrolyte.

Further, as understood from the following examples, it was found that the above fact also applied to a mixed solution containing electrolytes and nonelectrolytes other than the dialysate and that when a nonelectrolyte was added to and mixed with an electrolyte solution, the electric conductivity of the solution changed likewise.

EXAMPLE 1

6 gr of sodium chloride (electrolyte) was uniformly dissolved in one liter of water at 20° C. to prepare a sodium chloride water solution having a concentration of about 3.7 mol/liter. One liter of the sodium chloride water was poured into a glass vessel having a capacity of 1.5 liters and a pair of electrodes of an electric conductivity meter (made by TOA Electronics Ltd., Commodity Name "CM-40S") were dipped into the sodium chloride water solution.

Figure 1:
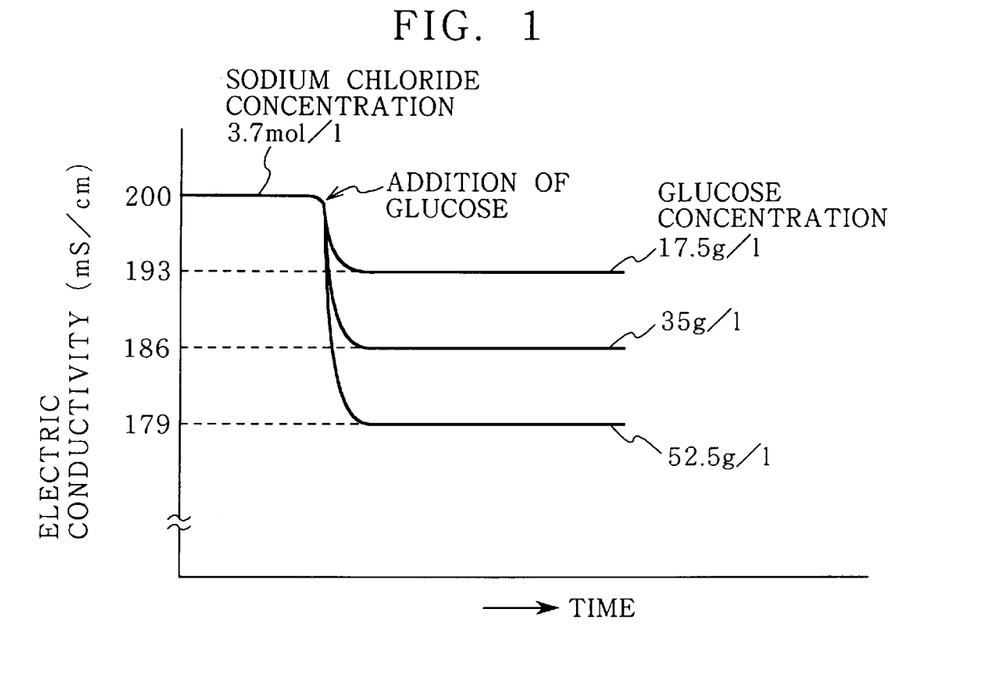
FIG. 1 is a graph showing the change in electric conductivity when glucose is added to a sodium chloride water solution.

Next, glucose powder was added to the sodium chloride water solution in the vessel so that the concentration of the glucose was set to about 17.5 gr/liter in a mixed water solution of the sodium chloride and the glucose, that is, about 17.5 gr glucose was added to one liter of the sodium chloride water solution, and the glucose and the water solution were stirred to be uniformly mixed together. On the other hand, an AC voltage (voltage between peaks) Vp-p= about 30 mV was imposed between the pair of electrodes of the electric conductivity meter and an electric current flowing between the electrodes was detected to thereby measure the electric conductivity of the mixed solution of the sodium chloride and the glucose. As shown in FIG. 1, although the electric conductivity of the mixed water solution lowered at first as time elapsed by the addition of the glucose, it took a constant value after a predetermined period of time had elapsed.

Thereafter, another 17.5 gr of glucose were added two more times (that is, the concentration of the glucose was set to about 35 gr/liter and about 52.5 gr/liter) and the electric conductivity of the mixed water solution was measured. As shown in FIG. 1, although the electric conductivity of the mixed water solution also lowered at first as time elapsed, it had a constant value after a predetermined period of time had elapsed.

Figure 2:
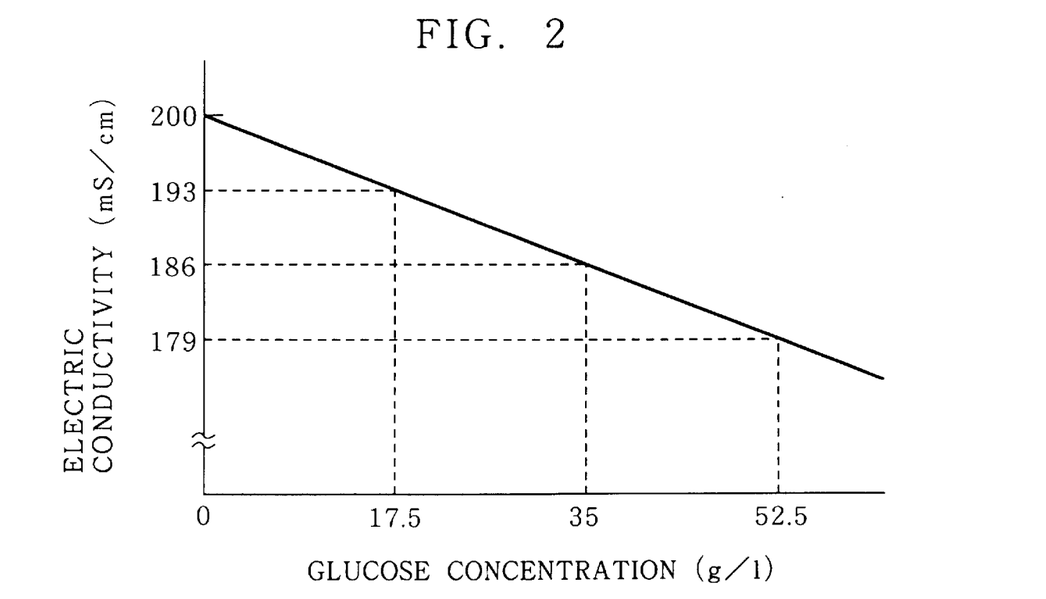
FIG. 2 is a graph showing the correlation between the concentration of glucose and the electric conductivity of a mixed water solution of sodium chloride and the glucose, determined in Example 1.

It is found from FIG. 1 that as the additive amount of the glucose increases, the electric conductivity of the mixed water solution lowers. FIG. 2 shows the relationship between the additive amount of the glucose, i.e. the concentration of the glucose and the electric conductivity of the mixed water solution of the sodium chloride and the glucose, wherein it is found that a fixed correlations i.e. a linear correlation exists between the concentration of the glucose and the electric conductivity.

EXAMPLE 2

About 289 gr of an electrolyte substance which excludes the glucose in the agent A of a dialysis solution was uniformly dissolved in one liter of water at 20° C. to prepare a water solution (referred to as an agent A electrolyte concentration of 4.4 mol/liter). The above-mentioned electrolyte substance contains sodium chloride (NaCl), potassium chloride (KCl), calcium chloride ($CaCl_2.2H_2O$), magnesium chloride ($MgCl_2$), and sodium acetate ($CH_3COONa$) in the ratio of $NaCl:KCl:CaCl_2.2H_2O:MgCl_2.6H_2O:CH_3COONa=1933:47:69:32:258$. One liter of the water solution was poured into a glass vessel with a capacity of 1.5 liters.

Figure 3:
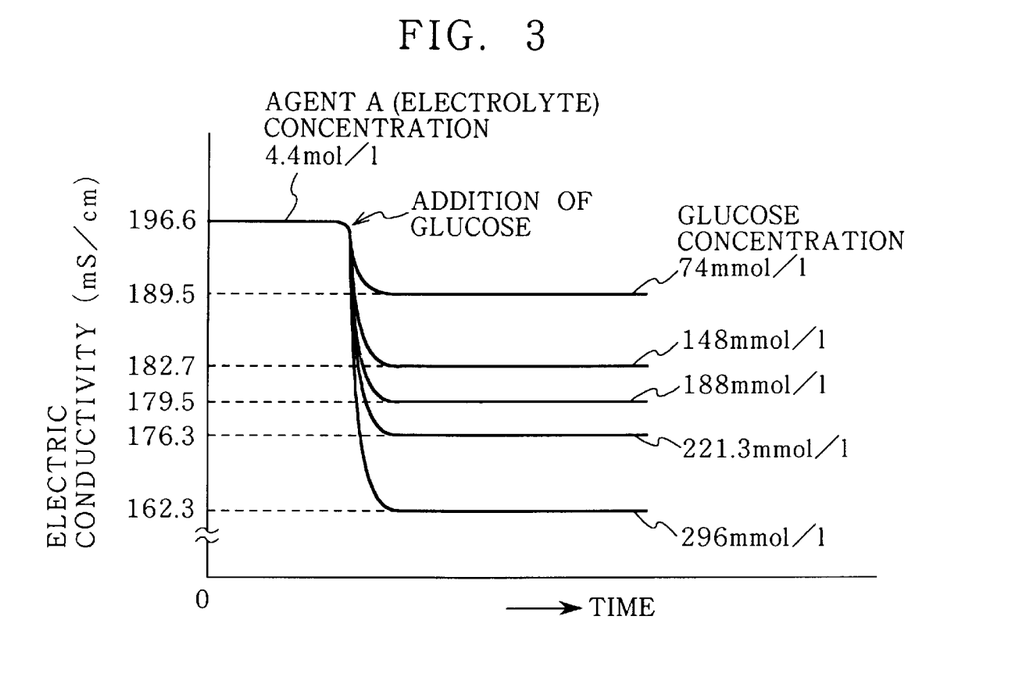
FIG. 3 is a graph showing the change in electric conductivity when glucose is added to a water solution of electrolytes excluding the glucose in the agent A of a dialysate.

Next, glucose powder was added to the water solution in the vessel so that the concentration of the glucose was set to about 74 mmol/liter in the mixed water solution of the electrolytes and the glucose, that is, about 13.4 gr glucose was added to one liter of the electrolyte water solution, and the glucose and the water solution were stirred to be uniformly mixed. Then, the electric conductivity of the mixed water solution was measured using the electric conductivity meter (made by TOA Electronics Ltd., Commodity Name "CM-40S") as in Example 1. As shown in FIG. 3, although the electric conductivity of the mixed water solution lowered at first as time elapsed, it had a constant value after a predetermined period of time had elapsed.

Thereafter, amounts of about 13.4 gr of glucose were added incrementally (that is, the concentration of the glucose was set to about 148, 188, 221.3 and 296 mmol/liter) and the electric conductivity of the mixed water solution was measured. As shown in FIG. 3, although the electric conductivity of the mixed water solution lowered at first as time elapsed, it took a constant value after a predetermined period of time had elapsed.

Figure 4:
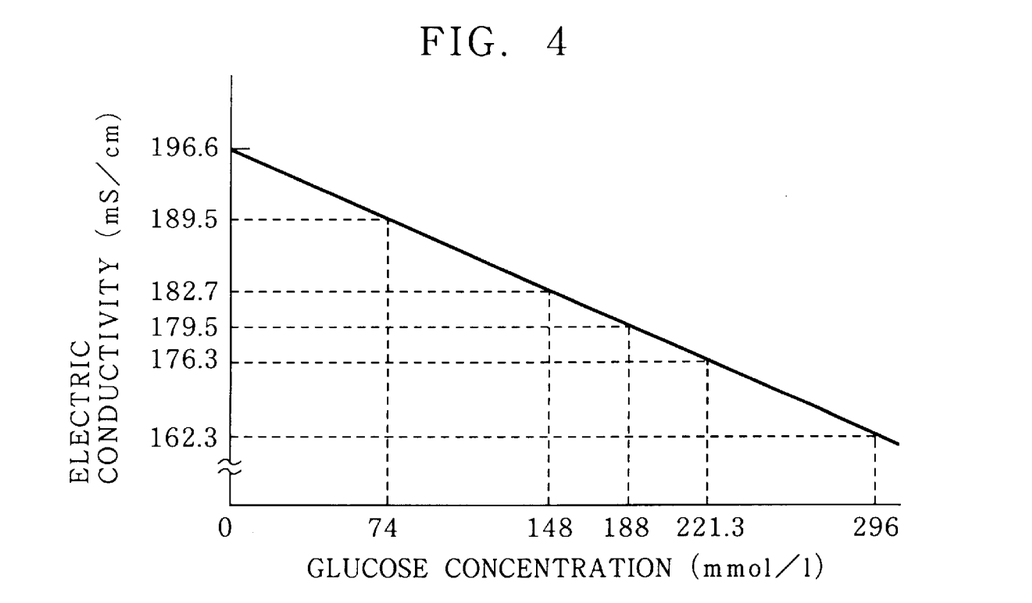
FIG. 4 is a graph showing the correlation between the concentration of glucose and the electric conductivity of a mixed water solution which contains electrolytes excluding the glucose in the agent A of a dialysate and the glucose, determined in Example 2.

It is found from FIG. 3 that as the additive amount of the glucose increases, the electric conductivity of the mixed water solution lowers. FIG. 4 shows the relationship between the additive amount of the glucose, i.e. the concentration of the glucose and the electric conductivity of the mixed water solution of the electrolytes and the glucose, wherein it is found that a fixed correlation, i.e. a linear correlation exists between the concentration of the glucose and the electric conductivity.

EXAMPLE 3

About 205 gr of sodium chloride was uniformly dissolved in one liter of water at 20° C. to prepare a sodium chloride water solution having a concentration of about 3.5 mol/liter. One liter of the water solution was poured into a glass vessel having a capacity of 1.5 liter.

Figure 5:
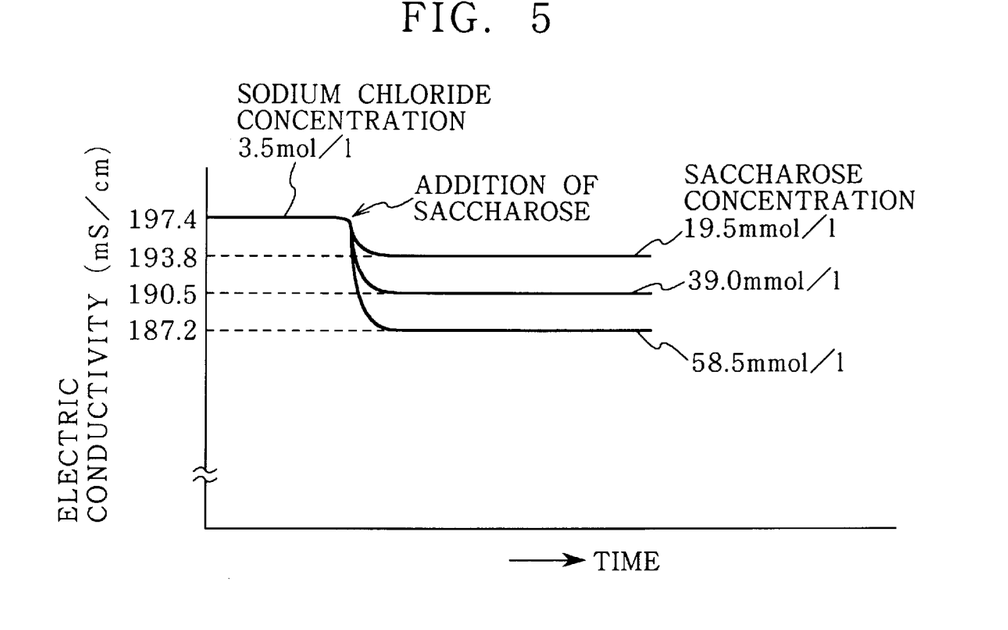
FIG. 5 is a graph showing the change in electric conductivity when saccharose is added to a sodium chloride water solution.

Next, cane sugar powder (saccharose) was added to the water solution in the vessel so that the concentration of the saccharose was set to about 19.5 mmol/liter in the mixed water solution of the sodium chloride and the saccharose, that is, about 6.7 gr saccharose was added to one liter of the sodium chloride water solution, and the saccharose and the water solution were stirred to be uniformly mixed together. Then, the electric conductivity of the mixed water solution was measured using the electric conductivity meter (made by TOA Electronics Ltd., Commodity Name "CM-40S") as in Example 1. As shown in FIG. 5, although the electric conductivity of the mixed water solution lowered at first as time elapsed, it had a constant value after a predetermined period of time had elapsed.

Thereafter, amounts of about 6.7 gr of saccharose were added incrementally (that is, the concentration of the saccharose was set to about 39.0 mmol/liter and about 58.5 mmol/liter) and the electric conductivity of the mixed water solution was measured. As shown in FIG. 5, although the electric conductivity of the mixed water solution lowered at first as time elapsed, it had a constant value after a predetermined period of time had elapsed.

Figure 6:
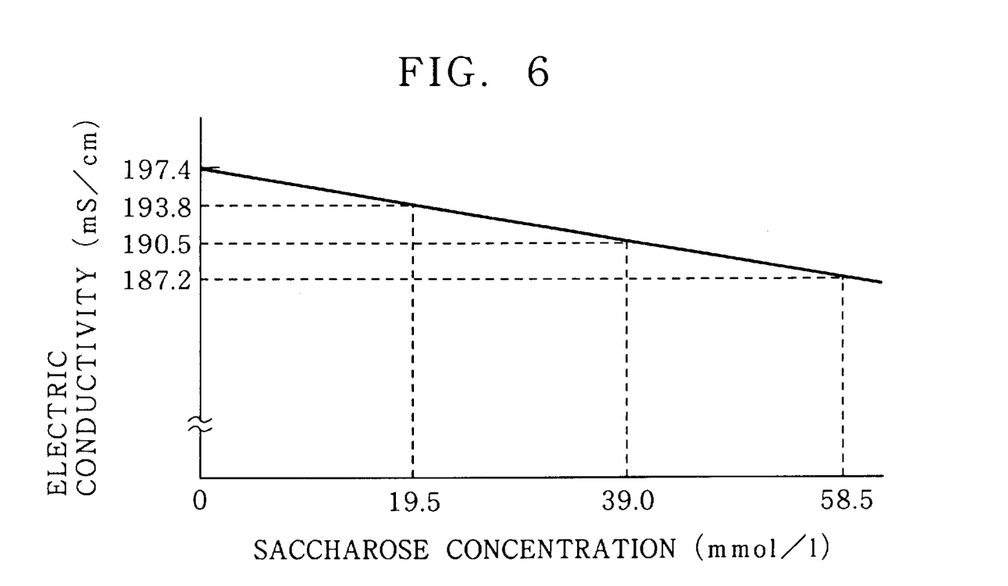
FIG. 6 is a graph showing the correlation between the concentration of saccharose and the electric conductivity of a mixed water solution of sodium chloride and the saccharose, determined in Example 3.

It is found from FIG. 5 that as the additive amount of the saccharose increases, the electric conductivity of the mixed water solution lowers. FIG. 6 shows the relationship between the additive amount of the saccharose, i.e. the concentration of the saccharose and the electric conductivity of the mixed water solution of the sodium chloride and the saccharose, wherein it is found that a fixed correlation, i.e. a linear correlation exists between the concentration of the saccharose and the electric conductivity.

EXAMPLE 4

About 163 gr of sodium chloride (two molecules of water of crystallization) was uniformly dissolved in one liter of water at 20° C. to prepare a sodium chloride water solution having a concentration of about 1.11 mol/liter. One liter of the water solution was poured into a glass vessel with a capacity of 1.5 liter.

Figure 7:
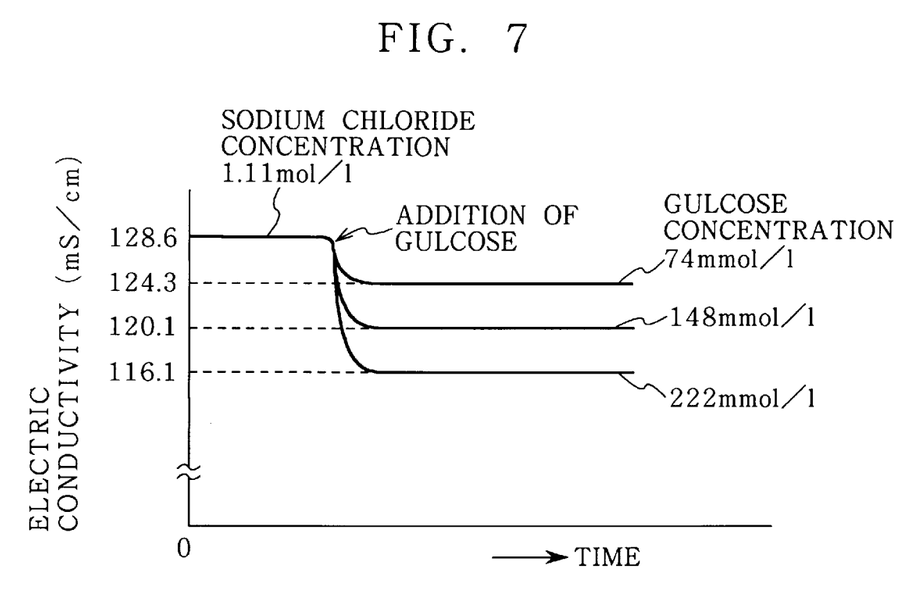
FIG. 7 is a graph showing the change in electric conductivity when glucose is added to a calcium chloride water solution.

Next, glucose powder was added to the water solution in the vessel so that the concentration of the glucose was set to about 74 mmol/liter in the mixed water solution of the calcium chloride and the glucose, that is, about 13.4 gr glucose was added to one liter of the calcium chloride water solution and, the glucose and the water solution were stirred to be uniformly mixed together Then, the electric conductivity of the mixed water solution was measured using the electric conductivity meter (made by TOA Electronics Ltd., Commodity Name "CM-40S") as in Example 1. As shown in FIG. 7, although the electric conductivity of the mixed water solution lowered at first as time elapsed, it had a constant value after a predetermined period of time had elapsed.

Thereafter, amounts of about 13.4 g of glucose was added incrementally (that is, the concentration of the glucose was set to about 148 mmol/liter and about 222 mmol/liter) and the electric conductivity of the mixed water solution was measured. As shown in FIG. 7, although the electric conductivity of the mixed water solution lowered at first as time elapsed, it had a constant value after a predetermined period of time had elapsed.

Figure 8:
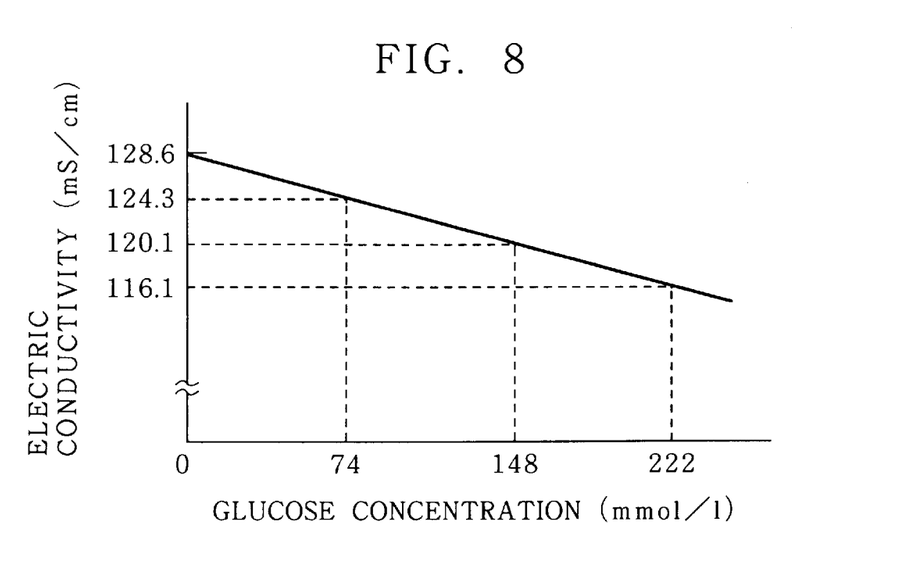
FIG. 8 is a graph showing the correlation between the concentration of glucose and the electric conductivity of a mixed water solution of calcium chloride and the glucose, determined in Example 4.

It is found from FIG. 7 that as the additive amount of the glucose increases, the electric conductivity of the mixed water solution lowers. FIG. 8 shows the relationship between the additive amount of the glucose, i.e. the concentration of the glucose and the electric conductivity of the mixed water solution of the calcium chloride and the glucose, wherein it is found that a fixed relative correlation, i.e. a linear correlation exists between the concentration of the glucose and the conductivity.

EXAMPLE 5

303 gr of the agent A of a dialysate was uniformly dissolved in one liter of water at 20° C. to prepare a water solution (referred to as an agent A concentration of 4.4 mol/liter). The above-mentioned agent A contains an electrolyte substance which is similar to that of Example 2 and is composed of sodium chloride (NaCl), potassium chloride (KCl), calcium chloride ($CaCl_2.2H_2O$), magnesium chloride ($MgCl_2$) and sodium acetate ($CH_3COONa$), and in addition glucose ($C_6H_{12}O_6$) in the ratio of $NaCl:KCl:CaCl_2.2H_2O: MgCl_2.6H_2O:CH_3COONa:C_6H_{12}O_6=$ 1933:47:69:32:258:315.

Figure 9:
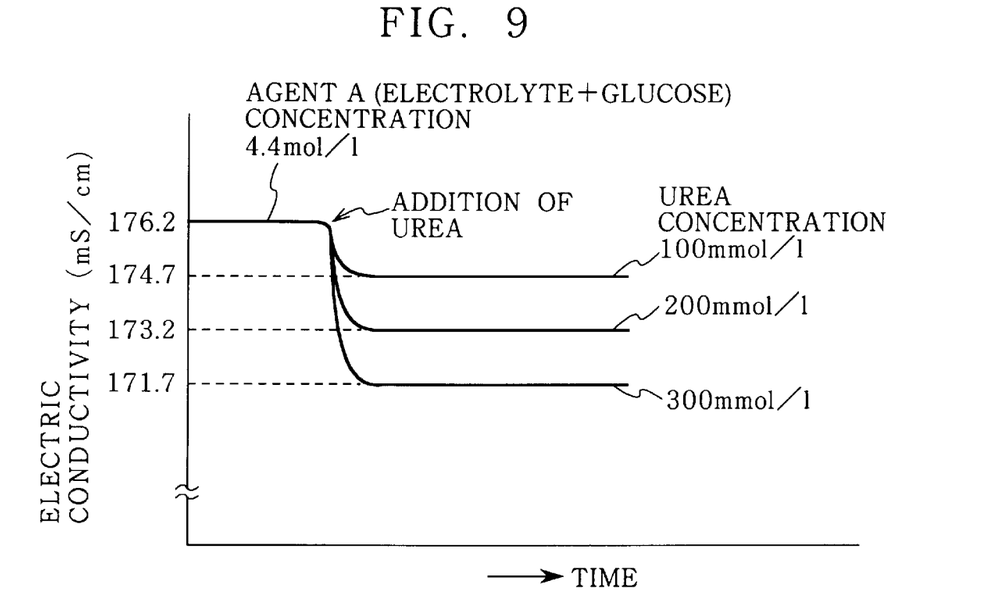
FIG. 9 is a graph showing the change in electric conductivity when urea is added to the water solution of the agent A (containing electrolytes and glucose) of a dialysate.

Next, urea was added to the water solution in the vessel so that the concentration of the urea was set to about 100 mmol/liter in the mixed water solution of the electrolyte and the urea, that is, about 6 gr urea was added to one liter of the electrolyte water solution, and the albumin and the water solution were stirred to be uniformly mixed together. Then, the electric conductivity of the mixed water solution was measured using the electric conductivity meter (made by TOA Electronics Ltd., Commodity Name "CM-40S") as in Example 1. As shown in FIG. 9, although the electric conductivity of the mixed water solution lowered at first as time elapsed, it had a constant value after a predetermined period of time had elapsed.

Thereafter, amounts of about 6 gr of urea were added incrementally (that is, the concentration of the urea was set to about 200 mmol/liter and about 300 mmol/liter) and the electric conductivity of the mixed water solutions were measured. As shown in FIG. 9, although the electric conductivity of the mixed water solution also lowered at first as time elapsed, it had a constant value after a predetermined period of time had elapsed.

Figure 10:
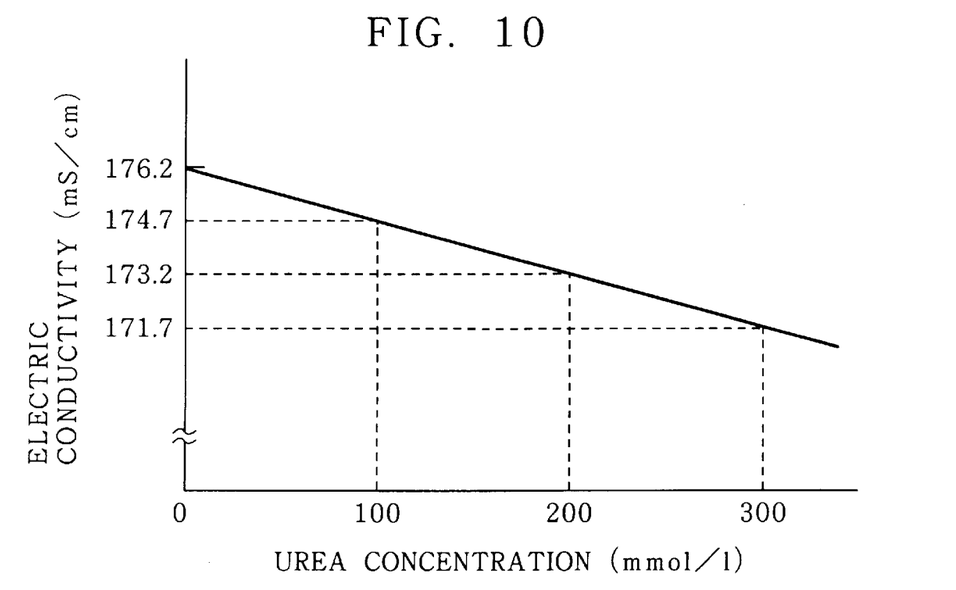
FIG. 10 is a graph showing the correlation between the concentration of urea and the electric conductivity of a mixed water solution of the agent A of a dialysate and the urea, determined in Example 5.

It is found from FIG. 9 that as the additive amount of the urea increases, the electric conductivity of the mixed water solution lowers. FIG. 10 shows the relationship between the additive amount of the urea, i.e. the concentration of the urea and the electric conductivity of the mixed water solution of the electrolyte and the urea, wherein it is found that a fixed correlation, i.e. a linear correlation exists between the concentration of the urea and the electric conductivity.

EXAMPLE 6

About 144 gr of an electrolyte substance which excludes the glucose in the agent A of a dialysis solution similar to that of Exmaple 2 was uniformly dissolved in one liter of water at 20° C. to prepare a water solution (referred to as an agent A electrolyte concentration of 2.2 mol/liter). The above-mentioned electrolyte substance contains sodium chloride (NaCl), potassium chloride (KCl), calcium chloride ($CaCl_2.2H_2O$), magnesium chloride ($MgCl_2$) and sodium acetate ($CH_3COONa$) in the ratio of $NaCl:KCl:CaCl_2.2H_2O:MgCl_2.6H_2O:CH_3COONa=$ 1933:47:69:32:258. One liter of the water solution was poured into a glass vessel with a capacity of 1.5 liters.

Figure 11:
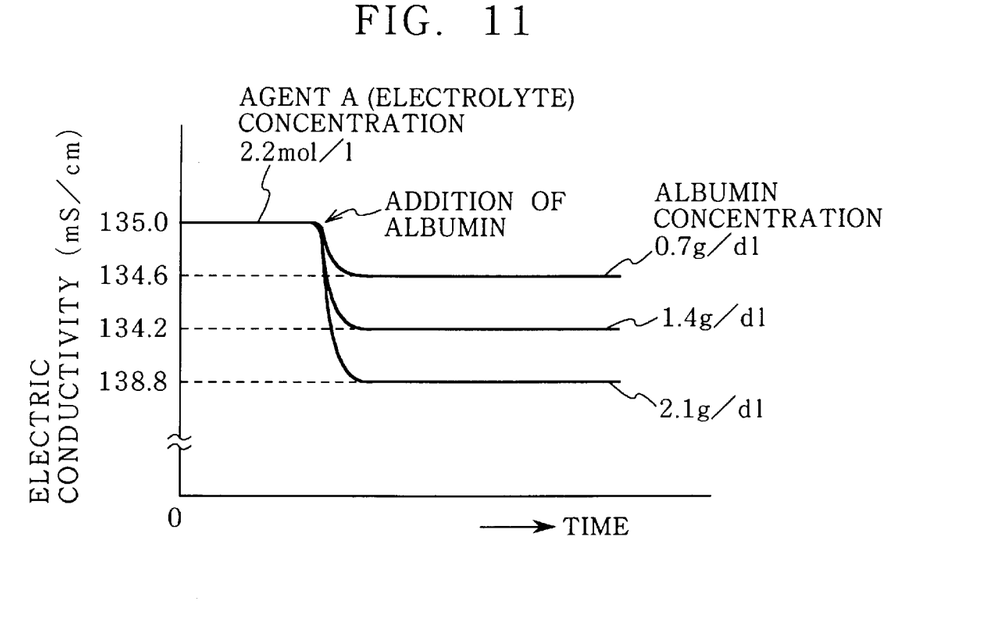
FIG. 11 is a graph showing the change in electric conductivity when albumin is added to a water solution of electrolytes excluding the glucose of the agent A of a dialysate.

Next, albumin (protein) was added to the water solution in the vessel so that the concentration of the albumin was set to about 0.7 gr/deciliter in the mixed water solution of the electrolytes and the albumin, that is, about 0.7 gr albumin was added, and the albumin and the water solution were stirred to be uniformly mixed together. Then, the electric conductivity of the mixed water solution was measured using the electric conductivity meter (made by TOA Electronics Ltd., Commodity Name "CM-40S") as in Example 1. As shown in FIG. 11, although the electric conductivity of the mixed water solution lowered at first as a time elapsed, it had a constant value after a predetermined period of time had elapsed.

Thereafter, amounts of about 0.7 gr of albumin were added incrementally (that is, the concentration of the albumin was set to about 1.4 gr/deciliter and about 2.1 gr/deciliter) and the electric conductivity of the mixed water solution was measured. As shown in FIG. 11, although the electric conductivity of the mixed water solutions also lowered at first as time elapsed, it had a constant value after a predetermined period of time had elapsed.

Figure 12:
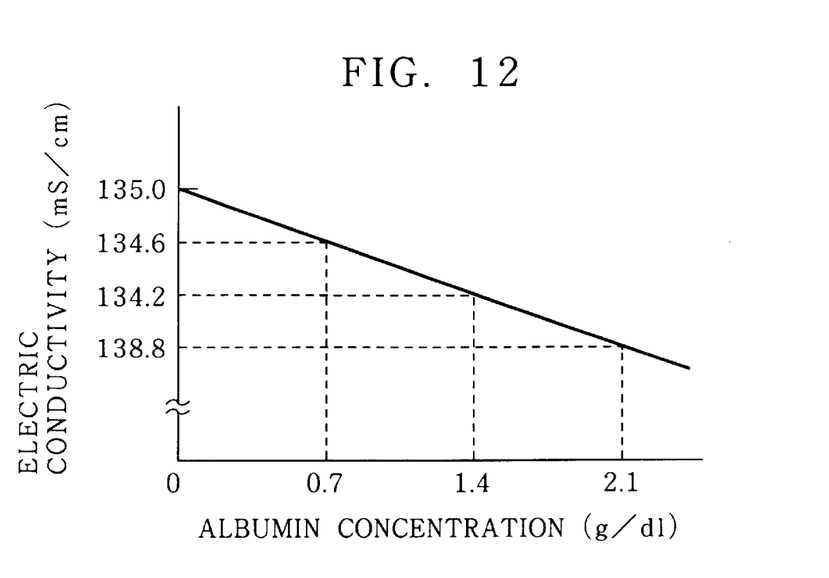
FIG. 12 is a graph showing the correlation between the concentration of albumin and the electric conductivity of a mixed water solution which contains electrolytes excluding the glucose of the agent A of a dialysate and the albumin, determined in Example 6.

It is found from FIG. 11 that as the additive amount of the albumin increases, the electric conductivity of the mixed water solution lowers. FIG. 12 shows the relationship between the additive amount of the albumin, i.e. the concentration of the albumin and the electric conductivity of the mixed water solution of the electrolyte and the albumin, wherein it is found that a fixed relative correlation, i.e. a linear correlation exists between the concentration of the albumin and the electric conductivity.

EXAMPLE 7

About 8.5 gr of an electrolyte substance which excludes the glucose in agent A of a dialysis solution similar to that of Example 2 was uniformly dissolved in one liter of water at 20° C. to prepare a water solution (referred to as an agent A electrolyte concentration of 0.13 mol/liter). The above-mentioned electrolyte substance contains sodium chloride (NaCl), potassium chloride (KCl), calcium chloride ($CaCl_2.2H_2O$), magnesium chloride ($MgCl_2$) and sodium acetate ($CH_3COONa$) in the ratio of $NaCl:KCl:CaCl_2.2H_2O MgCl_2.6H_2O:CH_3COONa=1933:47:69:32:258$. One liter of the water solution was poured into a glass vessel with a capacity of 1.5 liters.

Figure 13:
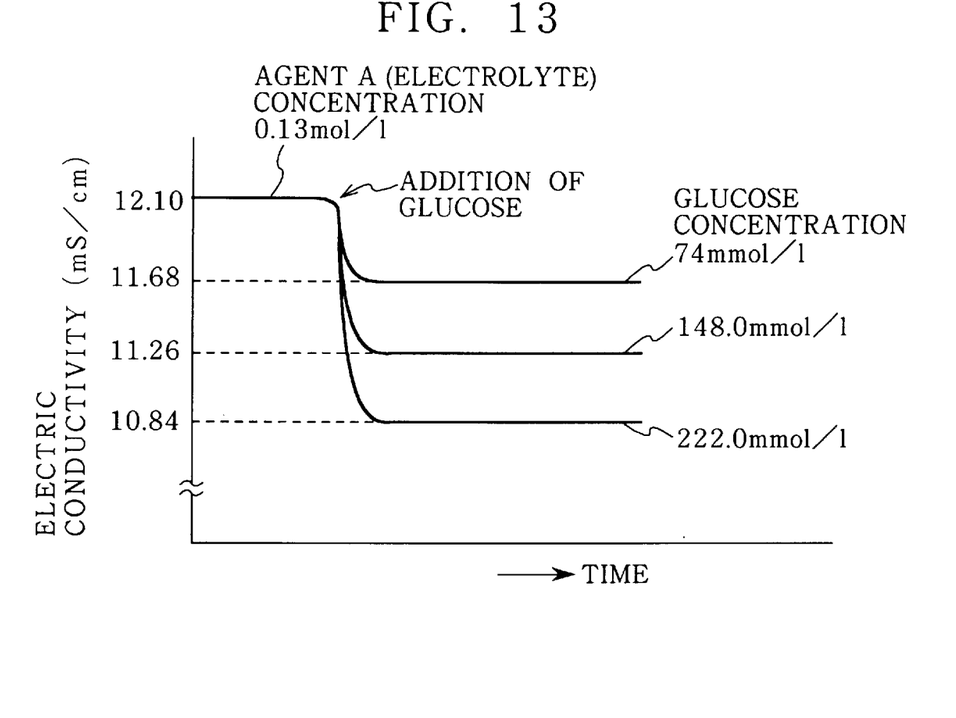
FIG. 13 is a graph showing the change in electric conductivity when glucose is added to a water solution of electrolytes excluding the glucose of the agent A of a dialysate.

Next, glucose powder was added to the water solution in the vessel so that the concentration of the glucose was set to about 74 mmol/liter in the mixed water solution of the electrolytes and the glucose, that is, about 13.4 gr glucose was added to one liter of the electrolyte water solution, and the powder glucose and the water solution were stirred to be uniformly mixed together. Then, the electric conductivity of the mixed water solution was measured using the electric conductivity meter (made by TOA Electronics Ltd., Commodity Name "CM-40S") as in Example 1. As shown in FIG. 13, although the electric conductivity of the mixed water solution lowered at first as time elapsed, it had a constant value after a predetermined period of time had elapsed.

Thereafter, amounts of about 13.4 gr of glucose were added incrementally to the vessel (that is, the concentration of the glucose was set to about 148.0 mmol/liter and about 222.0 mmol/liter) and the electric conductivity of the mixed water solution was measured. As shown in FIG. 13, although the electric conductivity of the mixed water solution lowered at first as time elapsed, it had a constant value after a predetermined period of time had elapsed.

Figure 14:
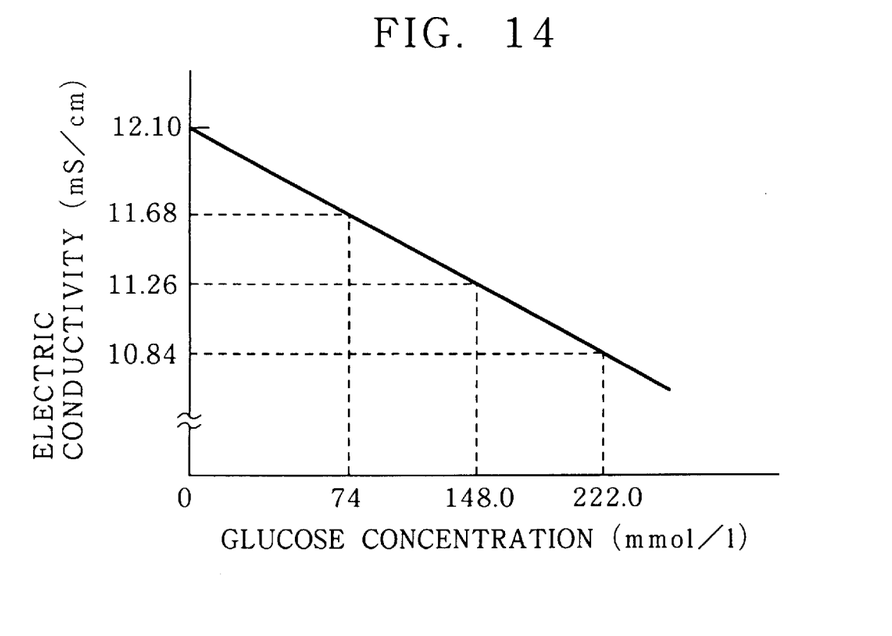
FIG. 14 is a graph showing the correlation between the concentration of glucose and the electric conductivity of a mixed water solution which contains electrolytes excluding the glucose of the agent A of a dialysate and the glucose, determined in Example 7.

It is found from FIG. 13 that as the additive amount of the glucose increases, the electric conductivity of the mixed water solution lowers. FIG. 14 shows the relationship between the additive amount of the glucose, i.e. the concentration of the glucose and the electric conductivity of the mixed water solution of the electrolytes and the glucose, wherein it is found that a fixed correlation, i.e. a linear correlation exists between the concentration of the glucose and the electric conductivity.

It can be understood from the above Examples 1–7 that there is the fixed linear correlation between the concentration of a nonelectrolyte in a mixed solution containing at least one electrolyte and the nonelectrolyte and the electric conductivity of said mixed solution.

The inventors have found based on the aforesaid novel knowledge that the concentration of a nonelectrolyte in a mixed solution containing at least one electrolyte and the nonelectrolyte can be measured by detecting the electric conductivity of the mixed solution. That is, according to the present invention, there is provided a measuring method in which the correlation between the electric conductivity and the concentration of a nonelectrolyte is determined as to the same mixed solution of electrolytes and nonelectrolytes, next the electric conductivity of a mixed solution containing the electrolytes and the nonelectrolytes whose concentration is unknown is measured and then the concentration of the nonelectrolyte in the mixed solution is determined from the thus obtained electric conductivity and the above correlation.

As described above, the method of measuring the concentration of a nonelectrolyte according to the present invention can directly and accurately measure the concentration of a nonelectrolyte such as sugar, protein, alcohol, amino acid or the like in a solution which coexists with electrolytes, by using an electric conductivity meter which is one of the most stable concentration detecting instruments having the least number of variable factors.

Since the electric conductivity changes with the change of the temperature of a solution, it is also required in the measuring method of the present invention that the measurement is conducted at a given constant temperature, for examples at 20° C. or at a temperature near 20° C. (for example, at 20° C.±0.5° C.). The electric conductivity meter used in the above respective examples (made by TOA Electronics Ltd., Commodity Name "CM-40S") was an electric conductivity meter having an automatic temperature compensation function which detects the temperature of the solution using a thermistor and sets a solution temperature coefficient to thereby decrease the change of electric conductivity due to the change in liquid temperature within a range corresponding to 0.5° C.

Since the electric conductivity itself cannot be measured when the concentration of electrolytes in a solution is too low, the concentration thereof must be sufficiently high to enable the measurement of the electric conductivity. For example, as to the measurement of the agent A of a dialysate, the concentration of the electrolytes in the undiluted water agent A is usually 0.1–5.5 mol/liter and measuring this high concentration is easily carried out by the method of the present invention.

Further, the method of measuring the concentration of a nonelectrolyte by electric conductivity according to the present invention is also applicable to the preparation of a mixed solution containing electrolytes and nonelectrolytes of a predetermined concentration. That is, a nonelectrolyte is added to and mixed with an electrolyte solution while continuously measuring the electric conductivity of the electrolyte solution, and then the concentration of the nonelectrolyte added to and mixed with the electrolyte solution is determined from the measured electric conductivity based on the correlation between the electric conductivity and the concentration of the nonelectrolyte determined previously as to the same system.

Therefore, when the electric conductivity detected by the electric conductivity meter reaches a predetermined value, the addition of the nonelectrolyte are stopped, thereby a mixed solution of the electrolytes and the nonelectrolytes having the target concentration of the nonelectrolytes can be obtained.

Next, a preparation method of a mixed solution containing electrolytes and a nonelectrolyte and an apparatus therefor will be described in detail.

EXAMPLE 8

In the present example, likewise to the description of Example 1, with respect to a mixed solution of sodium chloride as an electrolyte and glucose as a nonelectrolyte, the correlation between the concentration of the glucose and the electric conductivity shown in FIG. 2 was obtained by measuring the electric conductivity of the mixed solution of the sodium chloride and the glucose, using the electric conductivity meter (CM-40S) made by TOA Electronics Ltd. The concentration of the sodium chloride was fixed to 3.7 mol/liter (constant) and the measurement was conducted while changing the concentration of the glucose.

In the present example, a mixed water solution of an electrolyte (sodium chloride) and a nonelectrolyte (glucose) was prepared so that the concentration of the glucose was set to 35 gr/liter by adding and mixing glucose to and with the sodium chloride water solution which had a constant concentration similar to the above 3.7 mol/liter by the following operation.

That is, glucose powder was incrementally added to and mixed with a sodium chloride water solution having the same concentration of 3.7 mol/liter as the above while continuously measuring the electric conductivity of the water solution using the same electric conductivity meter as the above. Although the electric conductivity of the water solution containing only sodium chloride of the above concentration was 200 mS/cm, the measured electric conductivity of the water solution lowered as the additive amount of glucose increased.

According to the graph of FIG. 2 showing the predetermined correlation between the concentration of the glucose and the electric conductivity, since the electric conductivity at a target concentration of glucose of 35 gr/liter was 186 mS/cm, the addition of the glucose was stopped when the measured electric conductivity reached the above value (186 mS/cm).

The concentration of the glucose in the solution prepared in this example was measured to be 35 gr/liter by a glucose analyzer (glucose oxidase method) (Model GLU-1 made by TOA Electronics Ltd.). This measured concentration well coincided with the concentration of the glucose determined from the electric conductivity according to the present invention. Further, the reproducibility of the concentration of glucose was about ±1.4%.

EXAMPLE 9

Figure 15:
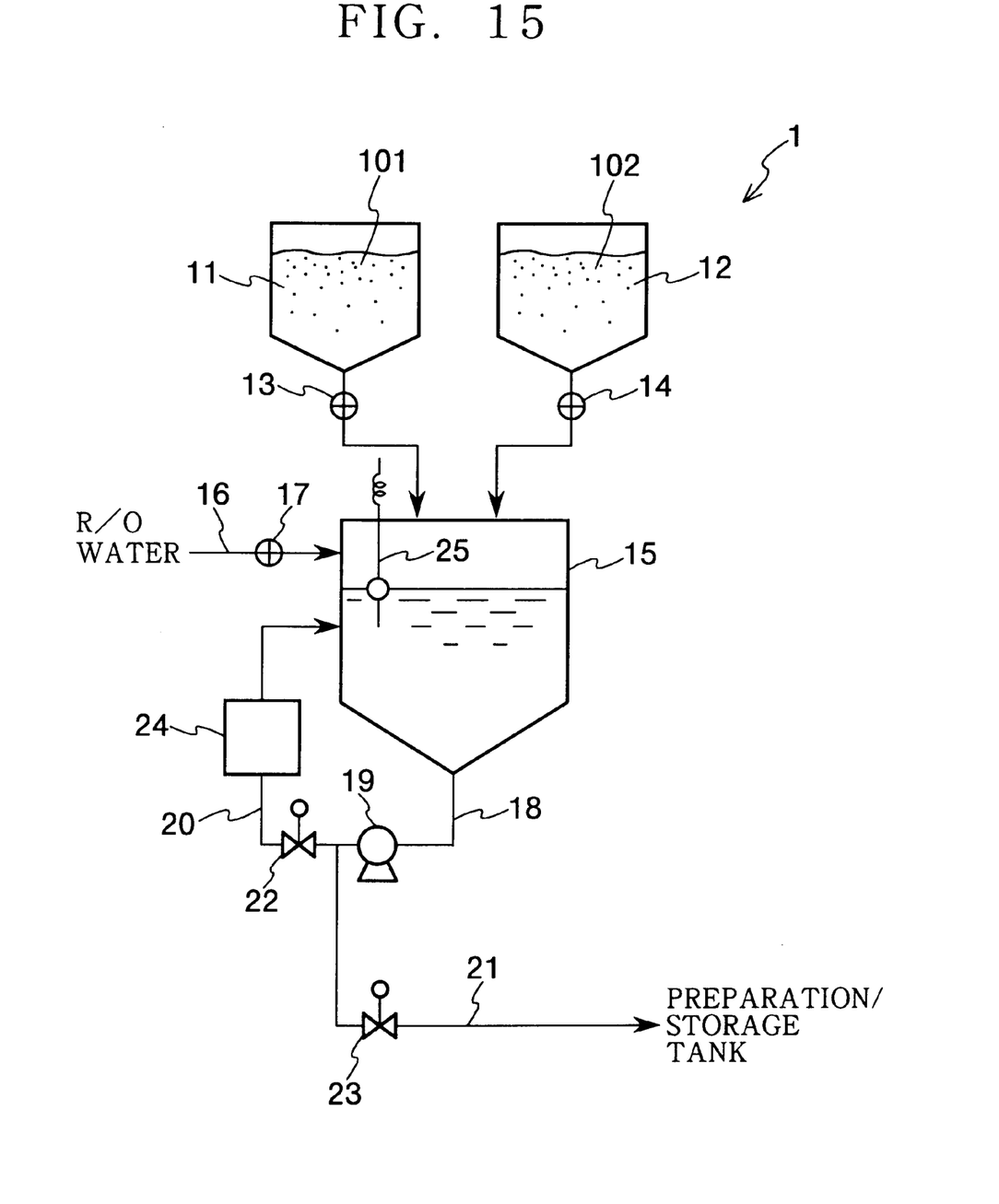
FIG. 15 is a view showing the schematic construction of an example of a preparation apparatus for a mixed solution containing electrolytes and nonelectrolytes of the present invention.

FIG. 15 shows the schematic arrangement of a preparation apparatus 1 for a dialysate, in particular, for the agent A as an embodiment of a preparation apparatus of the present invention.

The agent A preparation apparatus 1 includes a storage unit 11 such as a hopper storing electrolyte powder medicine 101 containing electrolytes excluding glucose of the agent A in a dialysate, that is, sodium chloride (NaCl), potassium chloride (KCl), calcium chloride ($CaCl_2.2H_2O$), magnesium chloride ($MgCl_2$) and sodium acetate ($CH_3COONa$) in the ratio of $NaCl:KCl:CaCl_2.2H_2O:MgCl_2.6H_2O:CH_3COONa=$ 1933:47:69:32:258, and a storage unit 12 such as a hopper storing glucose powder 102 as a nonelectrolyte. The electrolyte medicine 101 and the nonelectrolyte (glucose) medicine 102 are supplied from supply units 13 and 14 to a preparation tank 15, respectively. A pipe 16 is further connected to the preparation tank 15 and water is supplied to the tank through the pipe 16. The amount of water to be supplied is regulated by an electromagnetic valve 17.

Although the water may be tap water not containing bacterium, processed water such as R/O water (water processed by a reverse osmosis membrane) or the like is preferably used. Further, it is preferable to provide a warming device (not shown) with the preparation tank 15 to warm the tank 15 to about 25° C.–30° C. so as to shorten a dissolving time in the supplied R/O water in a colder season.

The water, electrolyte medicine 101 and glucose medicine 102 supplied into the preparation tank 15 are mixed with one another to prepare a mixed water solution (agent A).

A pump 19 is connected to the outlet of the preparation tank 15 through a pipe 18. Connected to the pump 19 is a pipe 20 for returning the mixed water solution discharged from the preparation tank 15 to the same again and a pipe 21 for supplying the mixed water solution of a given concentration (agent A) prepared in the preparation tank 15 to a preparation/storage tank (not shown) or a dialysis apparatus (not shown) directly so as to mix it together with the agent B of the dialysate (sodium hydrogencarbonate water solution).

Electromagnetic valves 22 and 23 are disposed to the pipes 20 and 21, respectively, and the pipe 20 or the pipe 21 can be selectively used by switching the electromagnetic valves 22, 23.

An electric conductivity meter 24 is further disposed to the pipe 20 to measure the concentration of the electrolytes or the nonelectrolyte of the mixed water solution in the preparation tank 15. The aforesaid electric conductivity meter (made by TOA Electronics Ltd., Model "CM-40S") can be preferably used as the electric conductivity meter 24.

Next, operation of the preparation apparatus constructed as described above will be described. First, the electromagnetic valve 17 is opened and R/O water is introduced into the preparation tank 15 through the pipe 16. The amount of the water is measured by a metering unit 25 such as a float switch disposed in the preparation tank 15. When the amount of the water is measured, the pump 19 is operated with the valve 22 opened and the valve 23 closed. With this operation, the water in the preparation tank 15 is circulated through the pipes 18 and 20. Subsequently, the electrolyte medicine 101 is supplied from the hopper 11 into the preparation tank 15 through the supply unit 13. The electrolyte medicine 101 is stirred and mixed by the circulating water in the preparation tank 15. Therefore, the electric conductivity meter 24 disposed in the pipe 20 can measure the concentration of the electrolyte mixed water solution flowing in the pipe 20. The electrolyte medicine 101 is supplied into the preparation tank 15 as necessary in response to the indication of the electric conductivity meter 24 so as to prepare an electrolyte water solution mainly composed of sodium chloride of a given concentration.

After the electrolyte water solution mainly composed of sodium chloride of the given concentration is prepared in the preparation tank 15, each given amount of the glucose powder medicine 102 is incrementally supplied from the hopper 12 into the preparation tank 15 through the supply unit 14. The electrolyte water solution and the glucose in the preparation tank 15 are sufficiently stirred by being circulated and flown through the pipe 20 by the pump 19, so that a mixed water solution of the electrolytes and the glucose is prepared. The concentration of the glucose in the mixed water solution of the electrolytes and the glucose in the preparation tank 15 can be measured by the electric conductivity meter 24 disposed in the pipe 20 when the water solution flows through the pipe 20.

That is, as to the agent A of a dialysate as shown, for example, in FIG. 4, the correlation between the electric conductivity of a mixed water solution and the concentration of the glucose (nonelectrolyte) is determined when the glucose is added to an electrolyte water solution mainly composed of sodium chloride of a predetermined concentration, and next the electric conductivity of a mixed water solution containing the electrolytes and the nonelectrolyte whose concentration is unknown is measured, then the concentration of the glucose in the mixed solution can be measured from the thus obtained electric conductivity and the above correlation.

When the mixed water solution containing the glucose of a predetermined concentration is prepared in the preparation tank 15, the valve 22 is closed and the valve 23 is opened so that the mixed water solution (agent A) set to the predetermined concentration in the preparation tank 15 is supplied to the preparation/storage tank (not shown) or the like while flowing through the pipe 21. An electrolyte solution (agent B) composed of sodium hydrogencarbonate of a given concentration prepared by another apparatus is supplied into the preparation/storage tank, so that a dialysate of a given concentration or an undiluted dialysate is prepared.

EXAMPLE 10

Figure 16:
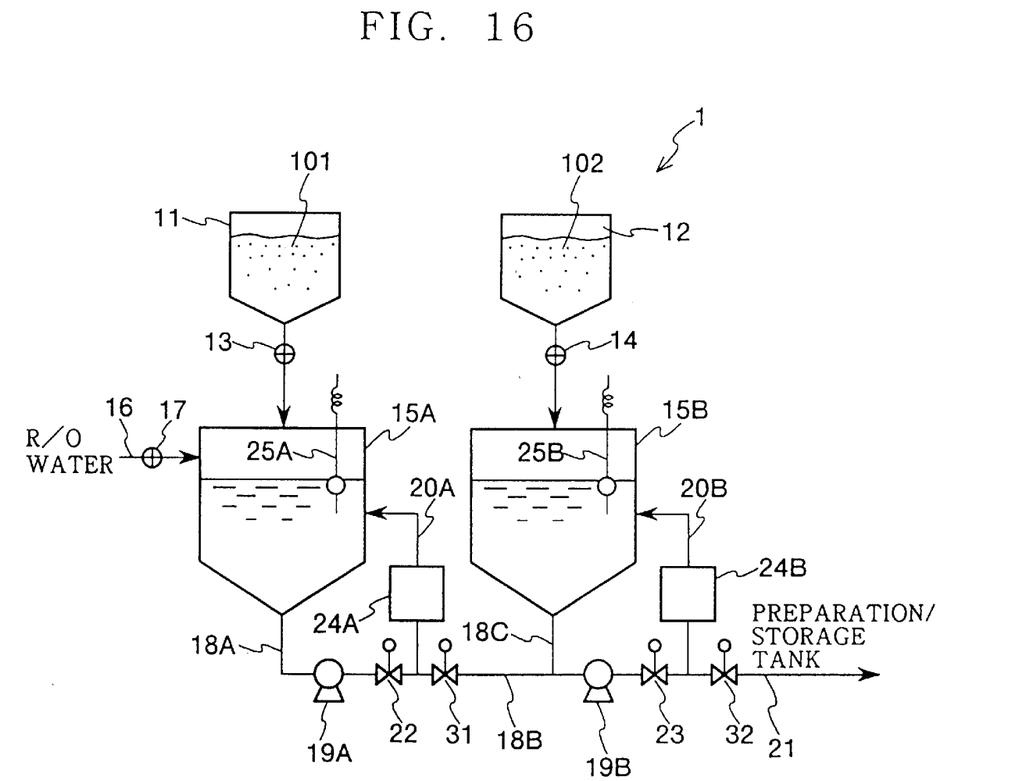
FIG. 16 is a view showing the schematic arrangement of another example of a preparation apparatus for a mixed solution containing electrolytes and nonelectrolytes of the present invention.

FIG. 16 shows another example of the preparation apparatus. Although the present example is a preparation apparatus 1 for a dialysate and in particular for the agent A of the dialysate as in Example 9, the present example is different from Example 9 in that preparation tanks 15 (15A, 15B) are provided for an electrolyte medicine 101 and a nonelectrolyte (glucose) medicine 102, respectively. Therefore, the members of the present example whose functions are similar to those of the preparation apparatus of Example 9 are denoted by the same numerals as used in Example 9 and a detailed description thereof is omitted.

Operation of the preparation apparatus 1 of the present example will be described. First, an electromagnetic valve 17 is opened and R/O water is introduced into the preparation tank 15A through a pipe 16. The amount of water is metered by a float switch 25A. When the desired amount of water is measured, a pump 19A is operated in the state that a valve 22 is opened and a valve 31 is closed. With this operation, the water in the preparation tank 15A is circulated through pipes 18A and 20A.

Subsequently, the electrolyte medicine 101 is supplied into the preparation tank 15A through a supply unit 13. The electrolyte medicine 101 is stirred and mixed by the circulating water. Therefore, the electric conductivity meter 24A disposed in the pipe 20A can measure the concentration of an electrolyte mixed water solution flowing through the pipe 20A. An electrolyte water solution mainly composed of sodium chloride of a given concentration is prepared by the electrolyte medicine 101 supplied into the preparation tank 15A as necessary in response to the indication of the electric conductivity meter 24A. When the electrolyte water solution mainly composed of the sodium chloride of the given concentration is prepared in the preparation tank 15A, the valve 31 and a valve 23 are opened, a valve 32 is closed and a pump 19B is operated. With this operation, the electrolyte water solution set to a given concentration in the preparation tank 15A is introduced into the preparation tank 15B. When it is detected by a float switch 25B that the predetermined amount of the electrolyte water solution has been introduced into the preparation tank 15B, the pump 19B is stopped and the valve 31 is closed.

Next, predetermined amounts of the glucose powder medicine 102 are incrementally supplied from a hopper 12 into the preparation tank 15B by a supply unit 14. The electrolyte water solution and the glucose in the preparation tank 15B are sufficiently stirred by being circulated by the pump 19B through a pipe 18C and a pipe 20B and made into a mixed water solution of the electrolytes and the glucose. The concentration of the glucose in the mixed water solution of the electrolytes and the glucose in the preparation tank 15B is measured by an electric conductivity meter 24B disposed in the pipe 20B by the same principle as that described in Example 9.

When the mixed water solution containing the glucose set to the given concentration (agent A) is prepared in the preparation tank 15B as described above, the valve 32 is opened so that the mixed water solution set to the given concentration in the preparation tank 15B is supplied to a preparation/storage tank (not shown) or the like by flowing through the pipe 21. As above, an electrolyte solution composed of sodium hydrogencarbonate of a predetermined concentration prepared by another apparatus (agent B) is supplied to the preparation/storage tank so that a dialysate of a given concentration or an undiluted dialysate is prepared.

It is contemplated in Example 9 described previously that in the case where the liquid supplying process is executed after the dissolving process or a rinsing process is executed prior to the dissolving process, a liquid remains in the pipes of the preparation tank when a process is switched, for example, from the rinsing process to the dissolving process. If the remaining liquid is mixed with a liquid having been dissolved, the concentration of the mixed liquid is somewhat different from that of the liquid in a dissolving tank. The construction of Example 10 solves this problem.

It is needless to say that the problem can be solved in such an apparatus as Example 9 by obtaining the amount of liquid remaining when a process is switched, providing a process which is operated prior to the start of the dissolving process and charging glucose in the prior process.

EXAMPLE 11

Figure 17:
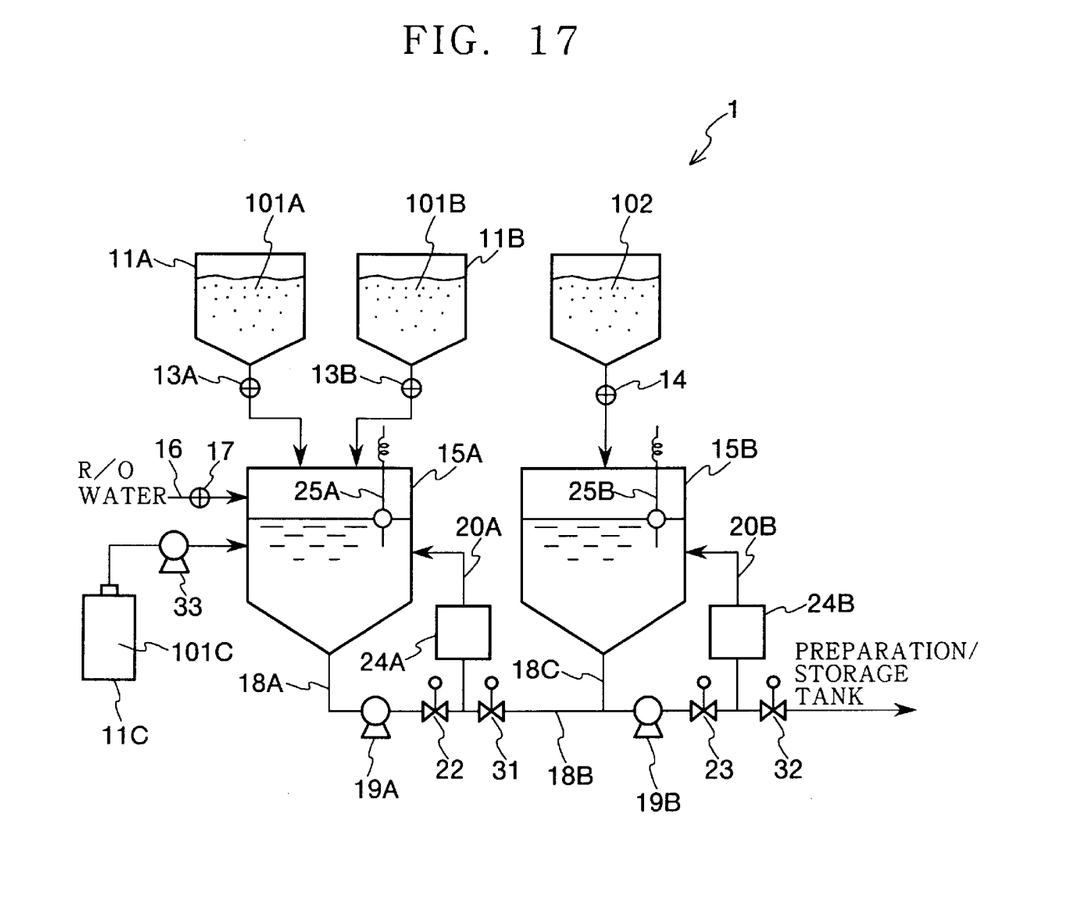
FIG. 17 is a view showing the schematic arrangement of still another example of a preparation apparatus for a mixed solution containing electrolytes and nonelectrolytes of the present invention.

FIG. 17 shows still another example of the preparation apparatus. Although the present example is a preparation apparatus 1 for a dialysate, in particular for an agent A as in Example 10, the present example is different from Example 10 in that in the preparation of an electrolyte medicine of a given concentration, a component to be added in a small amount such as potassium chloride, magnesium chloride etc. is premixed with a liquid agent, and in the preparation of an actual electrolyte water solution, other powder medicines to be added in a large amount are dissolved and mixed with the liquid agent in the preparation tank.

That is, in this example, potassium chloride, magnesium chloride etc. each of which is a small amount-component among electrolyte medicines, is previously prepared as a liquid agent 101C of a given concentration and filled in a vessel 11C and supplied from the vessel 11C to a preparation tank 15A. Further, among the electrolyte medicines, sodium chloride 101A is stored in a hopper 11A and sodium acetate 101B is stored in a hopper 11b in a powder state, respectively. In the apparatus of the present example, the members whose functions are similar to those of the preparation apparatus of Example 10 are denoted by the same numerals as used in Example 10 and the detailed description thereof is omitted.

To describe operation of the preparation apparatus 1 of the present example, first, an electromagnetic valve 17 is opened and R/O water is introduced into the preparation tank 15A through a pipe 16. The amount of the water is measured by a float switch 25A. On the completion of the measuring of the water, a pump 19A is operated in the state that a valve 22 is opened and a valve 31 is closed. With this operation, the water in the preparation tank 15A is circulated through a pipe 18A and a pipe 20A.

Subsequently, the small-amount-component 101C in the vessel 11C is supplied into the preparation tank 15A by a pump 33. The small-amount-component 101C is stirred and mixed by circulating water. Therefore, a conductivity meter 24A disposed in the pipe 20A can measure the concentration of the water solution of the small-amount-component flowing through the pipe 20A. The small-amount-component 101C is supplied into the preparation tank 15A as necessary in response to the indication of the conductivity meter 24A to thereby prepare the water solution of the small amounts of the components having a given concentration.

On the preparation of the water solution of the small-amount-component having the given concentration in the preparation tank 15A, a valve 33 is closed and the sodium chloride 101A among the electrolyte medicines is supplied from the hopper 11A into the preparation tank 15A through a supply unit 13A. The sodium chloride 101A is stirred and mixed by the circulating water solution of the small-amount-component. Therefore, the electric conductivity meter 24A disposed in the pipe 20A can measure the concentration of the electrolyte mixed water solution flowing through the pipe 20A. The sodium chloride 101A is supplied into the preparation tank 15A as necessary in response to the indication of the electric conductivity meter 24A to thereby prepare a mixed water solution of the small-amount-component and the sodium chloride having a given concentration.

Next, the sodium acetate 101B among the electrolyte medicines is supplied from a hopper 11B into the preparation tank 15A through a supply unit 13B. The sodium acetate 101B is stirred and mixed by the circulating water solution of the small-amount-component and the sodium chloride. Therefore, the electric conductivity meter 24A disposed in the pipe 20A can measure the concentration of the electrolyte mixed water solution flowing through the pipe 20A. The sodium acetate 101B is supplied into the preparation tank 15A as necessary in response to the indication of the electric conductivity meter 24A to thereby prepare a mixed water solution of the small-amount-component, sodium chloride and sodium acetate having a given concentration, that is, an electrolyte water solution.

A method of mixing the thus prepared electrolyte water solution having a given concentration with glucose after the preparation is the same as that of Example 10.

According to the present example, the apparatus can be reduced in size, and further, an economical merit can be obtained because a medicine (agent A) whose components are regulated to a predetermined mixing ratio is not necessary.

INDUSTRIAL APPLICABILITY

As described above, the method of measuring the concentration of a nonelectrolyte in an electrolyte solution according to the present invention can accomplish the direct and accurate measurement of the concentration of nonelectrolytes in a solution which contains electrolytes and nonelectrolytes, by using a simple instrument. Further, the preparation method and the preparation apparatus according to the present invention can achieve the simple and accurate preparation of a mixed solution containing nonelectrolytes of a given concentration by measuring the concentration of the nonelectrolytes in a solution which contains electrolytes and nonelectrolytes.

In particular, according to the present invention, there is provided a measuring method of directly and accurately measuring the concentration of the nonelectrolyte in the agent A of a dialysate which contains electrolytes and the nonelectrolyte by using a simple instrument, and in addition a preparation method and a preparation apparatus capable of simply and accurately preparing a water solution of the agent A containing a nonelectrolyte of a given concentration by measuring the concentration of the nonelectrolyte in the agent A making use of the above measuring method.

We claim:

1. A method of measuring a concentration of a nonelectrolyte in an electrolyte, comprising the steps of:

(a) adding stepwise and mixing a nonelectrolyte to and with an electrolyte solution which contains at least one electrolyte at a high concentration level sufficient such that an electric conductivity of the electrolyte solution is measurable, and measuring a reduction of the electric conductivity of the electrolyte solution into which the nonelectrolyte was added and with which the nonelectrolyte was mixed for each concentration of the nonelectrolyte, whereby a correlation between the electric conductivity of the electrolyte solution containing the nonelectrolyte and the concentration of the nonelectrolyte is determined for a system of the electrolyte and the nonelectrolyte;

(b) using the same system as step (a), adding and mixing the nonelectrolyte to and with a second solution of the electrolyte, and measuring the electric conductivity of the second solution of the electrolyte to which the nonelectrolyte was added and with which the nonelectrolyte was mixed; and (c) determining a concentration of the nonelectrolyte contained in the second solution of the electrolyte based on the correlation between the electric conductivity of the electrolyte solution and the concentration of the nonelectrolyte determined in step (a).

2. A method according to claim 1, wherein the electrolyte is an electrolyte medicine mainly composed of sodium chloride and the nonelectrolyte is a glucose medicine.

\* \* \* \* \*